United States Patent [19]

Grivsky

[11] 4,309,444
[45] Jan. 5, 1982

[54] BIOLOGICALLY ACTIVE AMIDES

[75] Inventor: Eugene M. Grivsky, Chapel Hill, N.C.

[73] Assignee: Burroughs Wellcome Co., Research Triangle Park, N.C.

[21] Appl. No.: 129,126

[22] Filed: Mar. 10, 1980

Related U.S. Application Data

[63] Continuation of Ser. No. 916,277, Jun. 16, 1978, abandoned, which is a continuation-in-part of Ser. No. 712,318, Aug. 6, 1976, abandoned, which is a continuation-in-part of Ser. No. 811,892, Jun. 30, 1977, abandoned.

[30] Foreign Application Priority Data

Feb. 3, 1976 [GB] United Kingdom ............... 04169/76

[51] Int. Cl.³ .......................................... A61K 31/165
[52] U.S. Cl. .................................... 424/324; 564/182
[58] Field of Search ................... 424/324; 260/558 D, 260/558 R

[56] References Cited

FOREIGN PATENT DOCUMENTS 663903 12/1951 United Kingdom .

OTHER PUBLICATIONS

Van Heyningen et al., J. Med. Chem., vol. 9, pp. 675-681 (1966).

Primary Examiner—Stanley J. Friedman
Attorney, Agent, or Firm—Donald Brown

[57] ABSTRACT

Cinnamamides of formula (I),

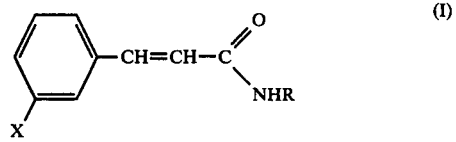

wherein X is fluoro, chloro, bromo, iodo or trifluoromethyl and R is branched alkyl, have anticonvulsant properties.

4 Claims, No Drawings

BIOLOGICALLY ACTIVE AMIDES

This is a continuation of application Ser. No. 916 277 filed June 16, 1978 which is a continuation-in-part of Ser. Nos. 712,318, filed Aug. 6, 1976 and 811,892 filed June 30, 1977 all are abandoned.

This invention is concerned with chemicals which have valuable pharmacological properties. In particular, the invention concerns cinnamamides, their synthesis, pharmaceutical preparations containing them, and their use in medicine.

It has been found that the cinnamamides of formula(I), as defined below, have anti-convulsant activity in mammals as is shown by their effects upon mice when administered to them in established pharmacological tests. These tests are:-
1. Maximal Electroshock Test (MES) in mice, a method described by Woodbury and Davenport, Arch int. Pharmacodyn. Ther. 92. P. 97–107 (1952).
2. Metrazol Seizure Test (MET) in mice, a method described by Swinyard, Brown and Goodman, J. Pharmacol. Exp. Therap. 106, 319–330 (1952).

In formula (I)

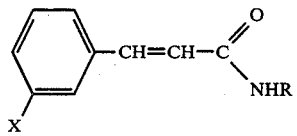

(I)

x is chlorine, bromine, fluorine, iodine or trifluoromethyl and R is branched alkyl having 4 to 8 carbon atoms.

The trans configuration of the compounds of formula (I) is preferred, and as a subclass among the compounds within the scope of this formula may be mentioned those wherein R is an isobutyl group.

The most preferred compound of Formula (I) is trans 3-Chloro-N-isobutylcinnamamide.

Among the compounds within formula (I) may specifically be mentioned:
3-bromo-N-t-butylcinnamamide;
3-iodo-N-t-butylcinnamamide; and
3-bromo-N-iso-butylcinnamamide.

The compounds of formula (1) may be made by any method known for the synthesis of cinnamamides of analogous structure. For example they may be prepared by the acylation of an amine $RNH_2$ (wherein R is hydrogen or alkyl having 1 to 3 carbon atoms) by the corresponding acid of formula (II): m-X-$PhCH=CHCO_2H$ (wherein X has the meaning given for formula (1) or a reactive derivative thereof such as a thioester or an ester (e.g. an alkyl ester or thioester where the alkyl has e.g. 1 to 4 carbon atoms), an amide, an acid halide (e.g. an acid chloride) or an acid anhydride. A wide variety of reaction conditions may be employed depending upon the nature of the acylating agent, but in general the reactants may be refluxed together, preferably in an inert liquid medium such as ether, benzene, toluene or cyclohexane.

A most convenient method of synthesis is to react the acid chloride with the appropriate amine. Preferably one equivalent of the halide should be used with two or more equivalents of the amine, but the molar excess of the amine may be replaced by another base such as triethylamine, pyridine, dimethylaniline, or potassium or sodium carbonate. A wide variety of polar or nonpolar liquid media may be used including water, alkanols such as methanol, ethanol, etc., ether, dioxane, benzene, toluene, xylene, petroleum ether, cyclohexane, tetrahydrofuran, chloroform and carbon tetrachloride. A wide range of temperature conditions may be employed, for example from −10° C. to the reflux temperature of the reaction mixture.

The compounds of formula (I) may be further prepared directly from the corresponding alcohol or aldehyde of formula (III) and (IV) at a temperature below 10° C.

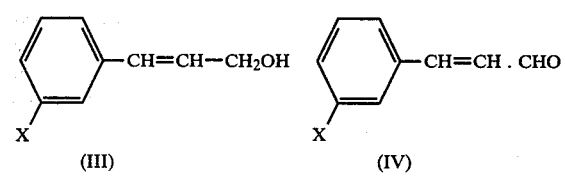

wherein X has the meaning in formula (I), by reaction with and an in a liquid medium such as ether, benzene, tetrahydrofuran, or a petroleum hydrocarbon.

The compounds of formula (I) may also be made by the reaction of an amide of formula (V):R.NH.W wherein W is a leaving group, for example —CO.H (a formamide), —CO.alkyl where the alkyl has eg. 1 to 4 carbon atoms (an amide), —$COMH_2$ (urea), —COO.alkyl (urethane having 1–4 carbon atoms in the alkyl group), with an acid of formula (II) or a reactive derivative thereof, for example the acid anhydride or halide. When the anhydride is used, a catalytic amount of sulphuric acid is preferably included. The reactants are conveniently heated together in a liquid medium.

In a further method for making a compound of formula (I), water, a hydrogen halide or molecular halogen is eliminated from a compound of formula (VI)

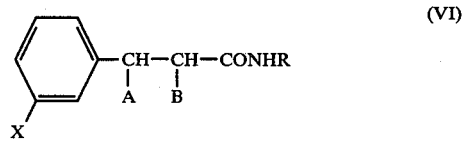

(VI)

wherein A and B are the same and each is halo or one of A and B is halo or hydroxy and the other is hydrogen, and X and R have the meaning given in formula (I) above. For example, the elimination of water from the α- or β-hydroxy compounds of formula (VI) may be effected by reaction with a dehydrating agent such as a base (eg. aqueous sodium hydroxide) or concentrated sulphuric or polyphosperic acid. The monohalo intermediates may be treated with a base (eg. potassium hydroxide or dimethylaniline) or merely heated to release the hydrogen halide. The dihalo intermediates may be reduced for example with zinc and ethanol is converted to the diiode compounds by treatment with potassium iodide with subsequent release of molecular iodine.

The intermediate acids of formula (II) may be made by classical organic synthetic methods such as the Perkin synthesis, the Reformatsky reaction and the Knosvenagel condensation.

The compounds of formula (I) may be used for the treatment or prophylaxis of convulsions of mammals such as mice, dogs, and cats, more importantly of man. In particular they may be used in the treatment of grand mal, petit mal, psychomotor epilepsy and focal seizures at a dose of 2 to 200 mg/kg of body weight per day. The optimum dose of course will vary with the nature of the compound, the condition of the patient and the route of administration, but the preferred dose is in the range of 20 to 60 mg/kg, most conveniently 30 to 50 mg/kg body weight, per day. Administration of the desired daily dose is preferably in three divided doses. For example, convenient forms of administration include tablets each containing from 100 to 500 mg of a compound of formula (I).

For use in medicine the compounds of formula (I) may be administered as a pure chemical but are preferably presented with an acceptable carrier therefor as a pharmaceutical composition. The carrier must of course be 'acceptable' in the sense of being compatible with the other ingredients of the composition and not deleterious to the recipient or the composition. The carrier may be a solid or a liquid or a mixture of solid and liquid substances, and is preferably formulated with a compound of formula (I) as a unit-dose composition, for example a tablet, capsule or sachet for oral administration or a suppository for rectal administration. Other pharmaceutically active substances may also be present in compositions of the present invention, and the composition may be formulated by any of the well-known techniques of pharmacy consisting basically of admixture of its components. Unit-dose compositions, for oral, rectal or parenteral administration (vid. inf.), conveniently contain a compound of formula (I) in an amount in the range 100 to 500 mg. for oral administration, fine powders or granules of the compounds may contain diluents and dispersing and surface active agents, and may be presented in a draught in water or in a syrup; in capsules or cachets in the dry state or in an aqueous or non-aqueous suspension, when a suspending agent may also be included; in tablets, preferably made from granule of the active ingredient with a diluent, by compression with binders and lubricants; or in a suspension in water or a syrup or an oil or in a water/oil emulsion, when flavoring, preserving, suspending, thickening and emulsifying agents may also be included. The granules or the tablets may be coated, and the tablets may be scored.

For parenteral administration (by intramuscular or intraperitoneal injection), the compounds may be presented in unit dose or multi-dose containers in aqueous or non-aqueous injection solutions which may contain antioxidants, buffers, bacteriostats and solutes which render the compounds isoconic with the blood; or in aqueous or non-aqueous suspensions when suspending agents and thickening agents amy also be included; extemporaneous injection solutions and suspensions may be made from sterile powders, granules or tablets which may contain diluents, dispersing and surface active agents, binders and lubricants.

It will be understood from the foregoing description that what we will claim in accordance with this invention comprises any novel feature described herein, principally but not exclusively as follows:

(a) Novel compounds of formula (I) hereinabove defined.

(B) Novel compounds of formula (I) hereinabove defined having the trans configuration.

(C) The synthesis of a novel compound of formula (I) by any known method and in particular the methods specifically described above and including the reaction of an acid m-X-PhCH=CHCO$_2$H or a reactive derivative thereof with a compound of the formula R.NH.W wherein W is a leaving group and R and X have the meaning in formula (I).

(D) A pharmaceutical composition comprising a compound of formula (I) and a pharmaceutically acceptable carrier therefor.

(c) A method for the treatment or prophylaxis of convulsions of a mammal comprising the administration to the mammal of an anti-convulsant effective, non-toxic amount of a compound of formula (I).

The following Examples illustrate the present invention but should not be construed as in any way constituting a limitation thereof. All temperatures are in degrees Celsius.

Example 1 Trans 3-Bromo-N-isobutylcinnanamide

A mixture of trans 3-bromocinnamic acid (m.p. 177°–179° C; 11.4 g), thienyl chloride (11.9 g) and dry benzene (150 ml) was heated at reflux for 2 hours. Solvent and excess thienyl chloride were removed by distillation under reduced pressure leaving trans 3-bromocinnamoyl chloride (12.2 g), b.p. 100°–100.5°C/0.2 mm Hg.

A solution of trans 3-bromocinnamoyl chloride (12.2 g) in dry tolene (150 ml) was added dropwise (rapidly) with rapid stirring to a solution of isobutylamine (9.5 g) in dry ether (200 ml). The reaction mixture was stirred at ambient temperature for one hour and then heated at 30°–35° C. for 2 hours. The solvent and excess amine were removed at reduced pressure. The residue was triturated with water and then recrystallized from ethanol-water (1:10), giving white, crystalline trans 3-bromo-N-isobutylcinnanamide (12.8 g), m.p. 104°–105° C. Elemental analysis NMR and IR confirmed this structure. TLC gave one spot run on silica gel using 5:1 and using 3:1 hexane:ethanol.

EXAMPLE 2

A suppository was formulated from the following ingredients:

| | |
|---|---|
| trans 3-bromo-N-isobutylcinnamamide | 300 mg |
| cocoa butter | 2000 mg |

EXAMPLE 3

A soft gelatin capsule was filled with the following ingredients:

| | |
|---|---|
| trans 3-bromo-N-isobutylcinnamamide | 300 mg |
| lactose | 75 mg |
| starch, corn | 20 mg |
| fused silica | 2 mg |
| magnesium stearate | 3 mg |

EXAMPLE 4

A syrup suspension was prepared from the following ingredients:

| | |
|---|---|
| trans 3-bromo-N-isobutylcinnamamide | 300 mg |
| sodium carboxymethylcellulose | 20 mg |
| microcrystalline cellulose | 100 mg |
| glycerin | 500 mg |
| Polysorbate 50 | .10 mg |
| flavoring agent | q.s. |

| -continued | |
|---|---|
| preserving agent | 0.1% |
| sucrose syrup | q.s. to 5 ml |

EXAMPLE 5

A compressed tablet was prepared from the following:

| | |
|---|---|
| trans-3-bromo-N-isobutylcinnamamide | 300 mg |
| starch, corn | 50 mg |
| microcrystalline cellulose | 50 mg |
| stearic acid | 4 mg |
| magnesium stearate | 1 mg |
| fused silica | 1 mg |

EXAMPLE 6

In the MXS pharmacological test referred to herinbefore, trans 3-bromo-N-isobutylcinnamamide had an $ED_{50}$ (i.p.) in mice of 46 mg/kg.

EXAMPLE 7 TRANS 3-CHLORO-N-ISOBUTYLCINNAMAMIDE

A solution of 3-chlorocinnamoyl chloride (4g) in dry toluene (75 ml) was added with stirring to a solution of isobutylamine (12 ml) in dry benzene (200 ml). The reaction mixture was allowed to stand for 24 hours. The solvent was evaporated under reduced pressure and the residue thoroughly triturated with water, washed with dilute hydrochloric acid and then with water. The resulting crude product was recrystallized from ethanol-water (1:10) to give trans 3-chloro-N-isobutylcinnamamide (3.9 g), m.p. 111.5°–112.5° C. Elemental analysis, nmr and ir data were all consistent with the assigned structure. TLC gave one spot run on silica gel with 5:1 and 3:1 hexane:ethanol.

EXAMPLE 8

A compressed tablet is prepared from the following:

| | |
|---|---|
| trans 3-Chloro-N-isobutylcinnamamide | 300 mg |
| starch, corn | 50 mg |
| microcrystalline cellulose | 50 mg |
| stearic acid | 4 mg |
| magnesium sterate | 1 mg |

| -continued | |
|---|---|
| fused silica | 1 mg |

EXAMPLE 9

A syrup suspension is prepared from the following ingredients:

| | |
|---|---|
| trans 3-Chloro-N-isobutylcinnamamide | 300 mg |
| sodium carboxymethylcellulose | 20 mg |
| microcrystalline cellulose | 100 mg |
| glycerine | 500 mg |
| Polysorbate 80 | .10 ml |
| flavoring agent | q.s. |
| preserving agent | 0.1% |
| sucrose syrup | q.s. to 5 ml |

EXAMPLE 10

A soft gelatin capsule is filled with the following ingredients:

| | |
|---|---|
| trans 3-Chloro-N-isobutylcinnamamide | 300 mg |
| lactose | 75 mg |
| starch, corn | 20 mg |
| fused silica | 2 mg |
| magnesium stearate | 3 mg |

EXAMPLE 11

A suppository is formulated from the following ingredients:

| | |
|---|---|
| trans 3-Chloro-N-isobutylcinnamamide | 300 mg |
| cocoa butter | 2000 mg |

What I claim is:

1. The method of treating or prophylaxis for convulsions in a mammal comprising the administration to said mammal of an anticonvulsant effective, non-toxic amount of a compound of trans3-chloro-N-isobutylcinnamamide.

2. The method of claim 1 in which the amount is 2 to 200 mg/kg bodyweight per day.

3. The method of claim 1 in which the mammal is a human.

4. The method of claim 3 in which the amount is 2 to 200 mg/kg bodyweight per day.

* * * * *